United States Patent [19]

Iwasaki et al.

[11] Patent Number: 5,233,057
[45] Date of Patent: Aug. 3, 1993

[54] BIPHENYL DERIVATIVES, PROCESS FOR PREPARING THE SAME AND INTERMEDIATES THEREFOR

[75] Inventors: Tameo Iwasaki, Nishinomiya; Kazuhiko Kondo, Osaka; Yuzo Matsuoka, Toyonaka; Mamoru Matsumoto, Nara; Masaki Sugiura, Kawanishi, all of Japan

[73] Assignee: Tanabe Seiyaku Co., Ltd., Osaka, Japan

[21] Appl. No.: 955,133

[22] Filed: Oct. 1, 1992

Related U.S. Application Data

[62] Division of Ser. No. 821,215, Jan. 15, 1992, Pat. No. 5,182,404, which is a division of Ser. No. 529,792, May 29, 1990, Pat. No. 5,103,023.

[30] Foreign Application Priority Data

Jun. 2, 1989 [JP] Japan ................... 1-141988

[51] Int. Cl.$^5$ ................ C07D 319/18; C07D 321/10; C07D 317/64
[52] U.S. Cl. ................... 549/435; 549/442; 549/436; 549/362; 549/350
[58] Field of Search ............. 549/350, 362, 435, 436, 549/442

[56] References Cited

U.S. PATENT DOCUMENTS

| | | | |
|---|---|---|---|
| 4,849,448 | 7/1989 | Kimura et al. | 514/464 |
| 4,904,694 | 2/1990 | Matsuoka et al. | 514/464 |

FOREIGN PATENT DOCUMENTS

| | | |
|---|---|---|
| 0269754 | 3/1988 | European Pat. Off. |
| 0267970 | 5/1988 | European Pat. Off. |
| 60-209582 | 10/1985 | Japan |
| 62-277379 | 12/1987 | Japan |
| 62-294677 | 12/1987 | Japan |
| 63-88176 | 4/1988 | Japan |
| 63-192771 | 8/1988 | Japan |

OTHER PUBLICATIONS

Wunsche, C. et al., "Elektronestoss-Induzierte Alkyl-Und Wasserstoffwanderungen Bei Diphensaurederivaten", Tetrahedron 24:8 (1968), pp. 3407-3416.
Zhang et al., Chemical Abstracts 92:23, Jun. 7, 1982, p. 630, No. 1992255x.
Dallacker et al., Chemical Abstracts 102:13, Apr. 1, 1985, p. 700, No. 113343g.

Primary Examiner—Nicky Chan
Attorney, Agent, or Firm—Browdy and Neimark

[57] ABSTRACT

Novel biphenyl derivatives of the formula:

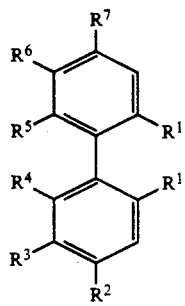

wherein $R^1$ is a substituted or unsubstituted aminocarbonyl group, aminothiocarbonyl group, a substituted or unsubstituted lower alkoxycarbonyl group, cyano group, or a group of the formula:

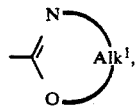

one or two of $R^2$ to $R^7$ are hydrogen atom, and the remaining groups are the same or different and are each a lower alkoxy group, a phenyl(lower)alkoxy group or hydroxy group, or the adjacent two groups thereof combine to form a lower alkylenedioxy group, and $Alk^1$ is a lower alkylene group, or a pharmaceutically acceptable salt thereof, which are useful for the prophylaxis and treatment of hepatic diseases, and processes for preparing the same, and intermediates therefor.

3 Claims, No Drawings

BIPHENYL DERIVATIVES, PROCESS FOR PREPARING THE SAME AND INTERMEDIATES THEREFOR

CROSS-REFERENCE TO RELATED APPLICATIONS

This is a division of application Ser. No. 07/821,215, filed on Jan. 15, 1992, now U.S. Pat. No. 5,182,404, which was a division of U.S. application Ser. No. 07/529,792, filed May 29, 1990, now U.S. Pat. No. 5,103,023.

FIELD OF THE INVENTION

This invention relates to novel biphenyl derivatives useful for prophylaxis and treatment of hepatic diseases, processes for preparing the same, and novel intermediates therefor.

PRIOR ART

The liver is an important organ which has various functions, for example, participates in various metabolisms, reserve of nutriments, and the like, but it is injured by various factors such as virus, drugs, alcohol, etc., and thereby induced into various hepatic diseases such as acute hepatitis, chronic hepatitis, fatty liver, etc. and finally hepatocirrhosis. It is known that these chronic hepatitis and hepatocirrhosis associated with cellular infiltration and hepatic fibrosis are one of intractable diseases.

As a drug for treating these hepatic diseases, there have been known symmetric octa-substituted biphenyl compounds such as dimethyl 4,4'-dimethoxy-5,6,5',6'-bis-(methylenedioxy)-2,2'-biphenyldicarboxylate (DDB) [cf. Japanese Patent First Publication (Kokai) No. 209582/1985].

Japanese Patent First Publication (Kokai) Nos. 294677/1987 and 88176/1988 disclose that the following octa-substituted biphenyl derivatives are effective for the treatment of hepatic diseases such as chronic or acute hepatitis.

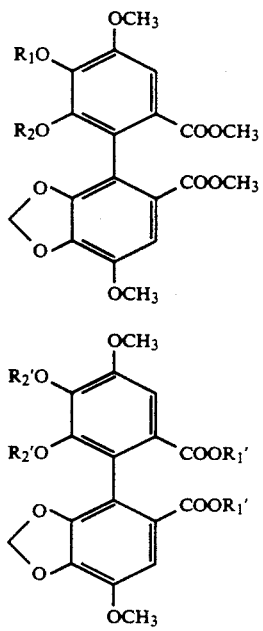

wherein $R_1$ and $R_2$ are methyl or both combine to form $O=C$, and $R_1'$ is hydrogen atom or a lower alkyl group and $R_2$ is a lower alkyl group.

SUMMARY DESCRIPTION OF THE INVENTION

The present inventors have intensively studied as to various substituted biphenyl derivatives and have found that novel hexa- or hepta-substituted biphenyl derivatives have excellent therapeutic and prophylactic effects on hepatic diseases.

An object of the invention is to provide novel hexa- or hepta-substituted biphenyl derivatives useful for the prophylaxis and treatment of various hepatic diseases. Another object of the invention is to provide processes for preparing the novel biphenyl derivatives. A further object of the invention is to provide a pharmaceutical composition for the prophylaxis and treatment of hepatic diseases containing as an active ingredient the novel biphenyl derivative. Still further object of the invention is to provide novel intermediate compounds useful for preparing the novel hexa- or hepta-substituted biphenyl derivatives. These and other objects and the advantages of the invention will be apparent to those skilled in the art from the following description.

DETAILED DESCRIPTION OF THE INVENTION

The novel hexa- or hepta-substituted biphenyl derivatives of the invention have the following formula:

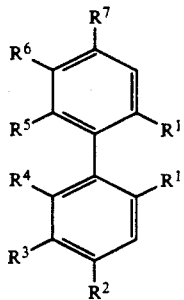

(I)

wherein $R^1$ is a substituted or unsubstituted aminocarbonyl group, aminothiocarbonyl group, a substituted or unsubstituted lower alkoxycarbonyl group, cyano group, or a group of the formula:

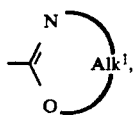

one or two of $R^2$ to $R^7$ are hydrogen atom, and the remaining groups are the same or different and are each a lower alkoxy group, a phenyl(lower)alkoxy group or hydroxy group, or the adjacent two groups thereof combine to form a lower alkylenedioxy group, and $Alk^1$ is a lower alkylene group.

In an embodiment of the invention, the biphenyl derivatives of the invention are the compounds of the formula (I) wherein $R^1$ is an aminocarbonyl group having optionally one or two substituents selected from a hydroxy(lower)alkyl group and a lower alkyl group; aminothiocarbonyl group; a lower alkoxycarbonyl group being optionally substituted by a lower alkoxy group; cyano group; or a 4,4-di(lower alkyl)-4,5-dihydro-2-oxazolyl group.

Preferred compounds are the compounds of the formula (I) wherein among $R^2$ to $R^4$, either one of $R^2$ and $R^4$ is hydrogen atom or a lower alkoxy group, and the remaining two groups are a lower alkoxy group, a phenyl(lower)alkoxy group or hydroxy group, or both combine to form a lower alkylenedioxy group; $R^5$ and $R^6$ combine to form a lower alkylenedioxy group; and $R^7$ is hydrogen atom.

More preferred compounds are the compounds of the formula (I) wherein (i) $R^2$ and $R^3$ are each a lower alkoxy or both combine to form a lower alkylenedioxy group, and $R^4$ is hydrogen atom;

(ii) $R^2$ is hydrogen atom, and $R^3$ and $R^4$ combine to form a lower alkylenedioxy group;

(iii) $R^2$ to $R^4$ are all a lower alkoxy group;

(iv) $R^2$ is a lower alkoxy group; $R^3$ and $R^4$ are combine to form a lower alkylenedioxy group, or $R^3$ is a phenyl(lower)alkoxy group and $R^4$ is hydrogen atom, or (v) $R^2$ is a lower alkoxy group, $R^3$ is hydroxy group, and $R^4$ is hydrogen atom;
and in any case of the above (i) to (v), $R^5$ and $R^6$ combine to form a lower alkylenedioxy group, and $R^7$ is hydrogen atom.

In the present specification, the lower alkyl group, lower alkoxy group and lower alkylene group denote alkyl group, alkoxy group and alkylene group consisting of each 1 to 6 carbon atoms, preferably 1 to 4 carbon atoms, respectively.

Among the compounds of this invention, the compounds of the formula (I) wherein $R^1$ is a substituted or unsubstituted aminocarbonyl group or a substituted or unsubstituted lower alkoxycarbonyl group can be prepared by reacting a biphenyldicarboxylic acid of the formula:

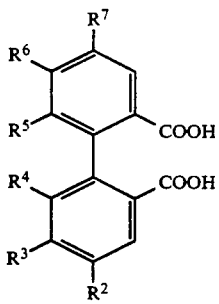
(II)

wherein $R^2$ to $R^7$ are as defined above, or a reactive derivative of the carboxyl groups thereof or a salt thereof with a compound of the formula:

$R^8$—H (III)

wherein $R^8$ is a substituted or unsubstituted amino group or a substituted or unsubstituted lower alkoxy group, or a salt thereof.

The compounds of the formula (I) wherein $R^1$ is a substituted or unsubstituted lower alkoxycarbonyl group can also be prepared by reacting a cyclic diester compound of the formula:

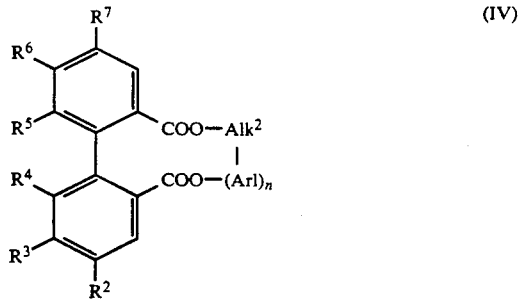
(IV)

wherein $Alk^2$ is a lower alkylene, Arl is an arylene group, n is 0 or 1, and $R^2$ to $R^7$ are as defined above, or a salt thereof with an alcohol compound of the formula:

$R^9$—H (V)

wherein $R^9$ is a substituted or unsubstituted lower alkoxy group.

The compounds of the formula (I) wherein $R^1$ is a group of the formula

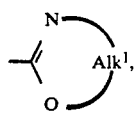

($Alk^1$ is as defined above) can be prepared by subjecting a bis(hydroxyalkylamide) compound of the formula:

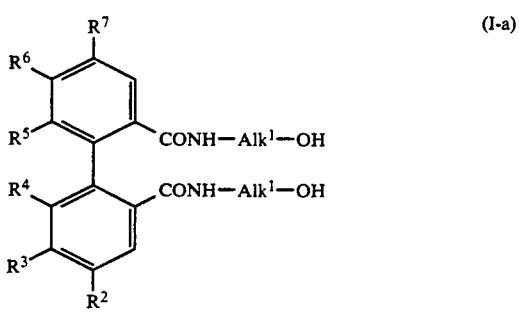
(I-a)

wherein $R^2$ to $R^7$ and $Alk^1$ are as defined above, or a reactive derivative thereof or a salt thereof to an intramolecular ring closure reaction.

The compounds of the formula (I) wherein $R^1$ is cyano group can be prepared by dehydrating a bis(carboxamide) compound of the formula:

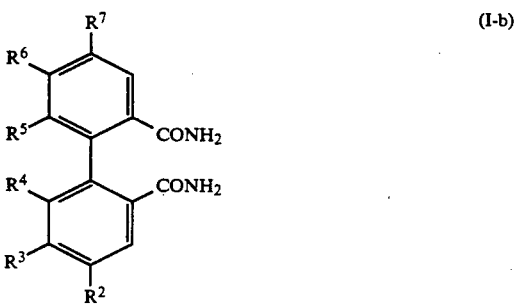
(I-b)

wherein $R^2$ to $R^7$ are as defined above, or a salt thereof.

Moreover, the compounds of the formula (I) wherein $R^1$ is aminothiocarbonyl group can be prepared by thiocarbonylation of the compound of the formula (I) wherein $R^1$ is cyano group, or a salt thereof.

The condensation reaction of a reactive derivative of the biphenyldicarboxylic acid compound (II) with the compound (III) can be carried out in an appropriate solvent in the presence or absence of an acid scavenger. The reactive derivative includes any conventional reactive derivative, for example, the corresponding acid halide, mixed acid anhydride, active ester, and the like. The acid scavenger includes, for example, pyridine, N,N-dialkylanilines, N-alkylmorpholins, alkali metal hydroxides, alkali metal carbonates, alkali metal hydrogen carbonates; trialkylamines in the presence or absence of N,N-dialkylaminopyridines, and the like. Besides, the condensation reaction of a free biphenyldicarboxylic acid compound (II) with the compound (III) can be carried out, for example, in the presence or absence of a condensation agent. The condensation agent includes any conventional condensation agent, for example, N,N'-dicyclohexylcarbodiimide, N-cyclohexyl-N'-morpholinocarbodiimide, N-ethyl-N'-(3-dimethylaminopropyl)carbodiimide, and the like. The above both condensation reactions are carried out in a conventional solvent such as dimethylformamide, dimethylacetamide, tetrahydrofuran, dichloromethane, ethyl acetate, acetonitrile, and the like, at a temperature of from cooling temperature to room temperature, for example, 0° to 20° C.

The reaction of the cyclic diester compound (IV) with the alcohol compound (V) can be carried out by a conventional ester exchange reaction, for example in the presence of an acid or a base in an appropriate solvent or without any solvent. The acid includes inorganic or organic acids such as sulfuric acid, hydrochloric acid, formic acid, acetic acid, p-toluenesulfonic acid, methanesulfonic acid, and the like, and the base includes organic or inorganic bases such as alkali metal hydroxides, alkaline earth metal hydroxides, alkali metal hydrides, and the like. The solvent includes lower alcohols, dioxane, tetrahydrofuran, diethyl ether, dimethylformamide, dimethylsulfoxide, acetonitrile, and the like. The reaction can be carried out at a warm or heat temperature, preferably at 30° to 80° C.

The intramolecular ring closure reaction of the bis(hydroxyalkylamide) compound (I-a) or a reactive derivative thereof can be carried out in the presence or absence of a halogenating agent in an appropriate solvent or without any solvent in a usual manner. The halogenating agent includes any conventional agent, for example, thionyl chloride, phosphorus pentachloride, phosphorus oxychloride, and the like. The solvent includes dichloromethane, dichloroethane, chloroform, and the like. The reaction preferably proceeds at a temperature of from cooling to room temperature, for example −20° C to 20° C.

The dehydrating reaction of the bis(carboxamide) compound (I-b) can be carried out in the presence or absence of a dehydrating agent. The dehydrating agent includes any conventional agent such as phosphorus oxychloride, thionyl chloride, phosphorus pentachloride, benzenesulfonic acid, aluminum chloride, and the like. The reaction can be carried out without using any solvent or in an appropriate solvent such as benzene, tetrahydrofuran, dimethylformamide, pyridine, and the like and preferably proceeds under heating, for example 60° to 100° C.

The thiocarbonylation of the compound of the formula (I) wherein $R^1$ is cyano group, can be carried out by treating the compound with a thiocarbonylation agent in an appropriate solvent in the presence or absence of an acid scavenger. The thiocarbonylation agent includes any conventional agents, for example hydrogen sulfide gas, phosphorus pentachloride, a dimer of p-methoxyphenylthionophosphinesulfide, and the like. The acid scavenger includes any substance as mentioned hereinbefore. The solvent includes preferably dioxane, pyridine, and the like. The reaction preferably proceeds at a temperature of from room temperature to heat temperature, for example at 20° to 100° C.

Besides, the compounds of the formula (I) wherein one of $R^2$ to $R^7$ is a phenyl(lower)alkoxy group (e.g. benzyl group) may be converted into the corresponding reduction products of the formula (I) wherein said group is hydroxy group. The reduction can be carried out by a conventional method, for example, by catalytic hydrogenation in hydrogen gas stream in the presence of an appropriate catalyst (e.g. palladium-carbon). The solvent includes any conventional solvent such as lower alkanols, dioxane, tetrahydrofuran, and the like. The reaction preferably proceeds under atmospheric pressure at a temperature of from room temperature to heat temperature, for example at 10° to 50° C.

In the above reactions, the starting compounds may be used as they stand or in the form of a salt thereof. For instance, the starting compounds of the formulae (II), (V) and (I-a) and of the formulae (III), (IV) and (I-b) which have a hydroxy group may be used in the form of an alkali metal salt, alkaline earth metal salt or ammonium salt, and the compounds of the formula (III) which have a substituted or unsubstituted amino group may be used in the form of an inorganic or organic acid addition salt.

The desired compounds (I) of this invention are novel and have excellent properties for the prophylaxis and treatment of hepatic diseases and can be used as a medicament. Specifically, the compounds (I) of this invention have excellent therapeutic, ameliorating and protecting effects on various hepatic damages such as denature and necrosis of hepatic cells, hepatic fibrosis, fatty retension, etc., and are useful as a therapeutic or prophylactic drug for chronic hepatitis, acute hepatitis, fatty liver, hepatic congestion, and hepatocirrhosis. For instance, a test compound was orally administered to mice and thereafter carbon tetrachloride was orally administered, and then increase of the blood plasma glutamic pyruvic transaminase (GPT), i.e., an index of hepatic disease, was measured. As a result, the object compounds (I) of this invention, dimethyl 5,6-methylenedioxy-4'-methoxy-5',6'-methylenedioxy-2,2'-bisphenyldicarboxylate and N,N,N',N'-tetraethyl-5,6-methylenedioxy-4',5'-dimethoxy-2,2'-biphenylbiscarboxamide showed 90 % or more inhibitory ratio of increase of the blood plasma GPT activity in a dose of 100 mg/kg.

The compounds (I) of this invention can be used as a drug either in a free form or in a form of a pharmaceutically acceptable salt thereof. The pharmaceutically acceptable salt includes inorganic or organic base salts, for example, alkali metal salts (e.g. sodium salt, potassium salt, etc.), alkaline earth metal salts (e.g. calcium salt, etc.), ammonium salts (e.g. tetramethylammonium salt, tetraethylammonium salt, etc.).

The compounds (I) of this invention can be administered orally or parenterally, but preferably orally. The compounds can be used in the form of a conventional pharmaceutical preparation, for example tablets, capsules, powders, and injections.

The dose of the compounds (I) may vary depending on the age, body weight or state of the patients, severity of the diseases and the like, but is usually in the range of 0.1 to 500 mg/kg/day, preferably 1 to 300 mg/kg/day.

The starting compounds of the formulae (II) and (IV) used in the process for preparing the desired compounds (I) of the invention can be prepared by condensing a 2-halogenobenzoic acid of the formulae:

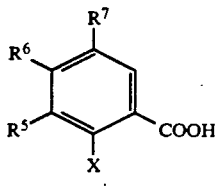 (VI)

and

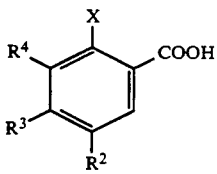 (VII)

wherein X is a halogen atom, and $R^2$ to $R^7$ are as defined above, or a reactive derivative thereof with a compound of the formula:

$HO-(Arl)_n-Alk^1-OH$ (VIII)

wherein Arl, n and $Alk^1$ are as defined above, to give a dihalogeno compound of the formula:

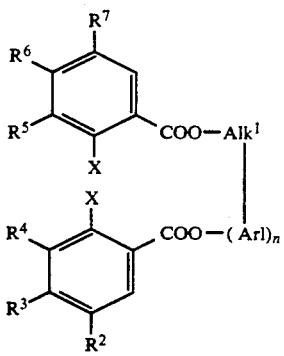 (IX)

wherein $R^2$ to $R^7$, $Alk^1$, Arl, and n are as defined above, and subjecting said compound (IX) to an intramolecular ring closure reaction, for example, in the presence of copper powder or copper(I) iodide, and the like, optionally followed by hydrolysis.

The compounds and preparation thereof of this invention are illustrated by the following Examples but should not be construed to be limited thereto.

EXAMPLE 1

(1-a) Piperonal (500 g) and cyclohexylamine (330 g) are dissolved in benzene, and the mixture is refluxed for about 3 hours while dehydrating with Diene Schtark device. The solvent is distilled off from the reaction mixture, and the residue is recrystallized from a mixture of isopropyl ether and hexane to give N-(3,4-methylenedioxybenzylidene)-N-cyclohexylamine (597 g).

The product (158 g) is dissolved in tetrahydrofuran. To the solution is added 2.5M n-butyllithium (30 ml) below −50° C., followed by dropwise addition of a solution of iodine (172 g) in tetrahydrofuran. The reaction mixture is warmed to room temperature and is poured into water. The precipitated crystals are separated by filtration, washed with water and dissolved in a mixture of dioxane, acetic acid and water. The mixture is allowed to stand at room temperature overnight. The solvent is distilled off from the mixture, and the residue is diluted with water. The precipitated crystals are collected by filtration, washed and dried to give 2-iodo-3,4-methylenedioxybenzaldehyde (118 g). M.p. 124°–126° C.

(1-b) 2-Bromo-4,5-dimethoxybenzaldehyde dimethylacetal (59 g) is dissolved in tetrahydrofuran and thereto is added 2.5M n-butyllithium (89 ml) under cooling at −70° C. The reaction mixture is kept below −50° C. for 30 minutes and thereto is added dropwise a solution of iodine (51.4 g) in tetrahydrofuran below −50° C. The mixture is kept at the same temperature for 15 minutes and thereto are added aqueous acetic acid to adjust the pH of the solution at 2. The mixture is allowed to stand at room temperature overnight, and the solvent is distilled off from the reaction mixture. The residue is dissolved in ethyl acetate. The solution is washed and dried, and the solvent is distilled off. The residue is crystallized from ethyl acetate to give 2-iodo-4,5-dimethoxybenzaldehyde (43 g). M.p. 139°–141° C.

(2-a) A solution of the product obtained in (1-a) (15 g) in dioxane (400 ml) and resorcinol (7.8 g) are added to 0.2N acetate buffer (200 ml), and thereto is gradually added sodium chlorite (5.9 g) with stirring. The mixture is stirred for 2 hours and then concentrated. The pH of the mixture is adjusted at 1 with conc. hydrochloric acid, and the precipitated crystals are separated by filtration, washed and dried to give 2-iodo-3,4-methylenedioxybenzoic acid (14 g).

The above product (13 g), thionyl chloride (16 ml) and pyridine (0.1 ml) are added to dioxane, and the mixture is refluxed for 30 minutes. The reaction mixture is distilled to remove the solvent and further subjected to azeotropic distillation with toluene to give 2-iodo-3,4-methylenedioxybenzoic chloride (14.5 g). M.p. 69°–70° C.

(2-b) The product obtained in (1-b) is treated in the same manner as described in (2-a) to give 2-iodo-4,5-dimethoxybenzoic chloride. M.p. 151°–154° C.

(3) Salicyl alcohol (22.4 g) is dissolved in dimethylacetamide (150 ml) and thereto are added triethylamine (64.1 ml) and 4-dimethylaminopyridiene (100 ml) under nitrogen gas stream, and the mixture is cooled to −30° C. To the mixture is added dropwise with stirring a suspension of the product obtained in (2-a) (62.1 g) in dimethylacetamide (100 ml) below −25° C. The mixture is stirred at the same temperature for 30 minutes and the reaction temperature is gradually raised up to room temperature. The mixture is further stirred for 5 hours at room temperature. After the reaction is over, the reaction mixture is cooled to −30° C. and thereto is added dropwise triethylamine (30.7 ml) followed by addition of a solution of the product obtained in (2-b) (52.8 g) in dimethylacetamide (100 ml). The mixture is stirred at room temperature overnight and is poured into a mixture of water-acetic acid. The organic layer is separated, washed, dried and distilled under reduced pressure to remove the solvent. The residue is recrystallized from toluene to give 2-iodo-3,4-methylenedioxybenzoic acid 2-[(2-iodo-4,5-dimethoxyphenyl)-carbonyloxy]benzyl ester (89.4 g). M.p. 128°–130° C.

(4) A suspension of copper powder (413 g) in dimethylformamide (1.5 liter) is refluxed with stirring. To the suspension is added dropwise a solution of the product obtained in (3) (89.5 g) in dimethylformamide (1000 ml) over a period of 3 hours, and the mixture is refluxed for 2 hours. Undissolved substances are filtered off from the reaction mixture, and the filtrate is concentrated under reduced pressure. To the residue is added ethyl acetate, and the mixture is washed with water, dried and distilled under reduced pressure to remove the solvent. The residue is recrystallized from toluene to give 5,6-methylenedioxy-5'-dimethoxy-2'-(2-hydroxymethyl-phenyloxycarbonyl)-2-biphenylcarboxylic acid lactone (53.7 g). M.p. 176°–179° C.

(5) The product obtained in (4) (1.5 g), ethyleneglycol monomethyl ether (30 ml) and sulfuric acid (1 ml) are heated at 110° C. for 60 hours. The reaction mixture is poured into a mixture of ethyl acetate (200 ml) and water (200 ml), and the organic layer is separated. The organic layer is washed, dried and distilled under reduced pressure to remove the solvent. The residue is purified with silica gel column chromatography [solvent, ethyl acetate-hexane (1:2)], and the eluate is distilled under reduced pressure to remove the solvent, and the residue is recrystallized from a mixture of diethyl ether-diisopropyl ether to give 5,6-methylenedioxy-4',5'-dimethoxy-2,2'-biphenyldicarboxylic acid bis(methoxyethyl) ester (900 mg) as colorless crystal. M.p. 59°–61° C.

EXAMPLE 2

(1) 2-Iodo-3,4-methylenedioxybenzoyl chloride (4.66 g), 1,3-propanediol (9.0 g) and 4-dimethylaminopyridine (50 ml) are dissolved in a mixture of tetrahydrofuran (70 ml) and triethylamine (4.21 ml), and the mixture is stirred at room temperature overnight. The reaction mixture is concentrated under reduced pressure, and the residue is extracted with methylene chloride. The solution is washed, dried and evaporated to dryness in vacuo to give colorless crystals (3.84 g). The crystals are dissolved in a mixture of tetrahydrofuran (50 ml) and triethylamine (2.95 ml). To the solution is added 4-dimethylaminopyridine (50 mg), followed by dropwise addition of a solution of 2-iodo-4,5-dimethoxybenzoyl chloride (3.5 g) in dimethylacetamide (50 ml) at −30° C. The mixture is stirred at room temperature overnight and poured into a mixture of water and ethyl acetate, and the organic layer is separated. The organic layer is washed, dried and concentrated under reduced pressure. The residue is recrystallized from ether to give 2-iodo-3,4-methylenedioxybenzoic acid 2-[(2-iodo-4,5-dimethoxyphenyl)carbonyloxy]propyl ester (4.82 g). M.p. 131°–133° C.

(2) The product obtained in (1) is treated in the same manner as in Example 1-(4) to give 5,6-methylenedioxy-4',5'-dimethoxy-2,2'-diphenyldicarboxylic acid trimethylene ester (1.8 g). M.p. 197°–199° C.

(3) The product obtained in (2) is treated in the same manner as in Example 1-(5) to give 5,6-methylenedioxy-4',5'-dimethoxy-2,2'-biphenyldicarboxylic acid bis(methoxyethyl) ester as colorless crystals.

This product has the same physicochemical properties as those of the product of Example 1.

EXAMPLES 3 TO 11

The corresponding starting compounds are treated in the same manner as in Example 1 or Example 2 to give the compounds as shown in Table 1.

TABLE 1

| Ex. No. | $R^2$ | $R^1$ | Physical properties, etc. |
|---|---|---|---|
| 3 | 4-methyl, 3-CH$_3$O, 2-CH$_3$O phenyl | —COOCH$_3$ | M.p. 121° C. |
| 4 | The same as above | —COOC$_2$H$_5$ | M.p. 82° C. |
| 5 | 4-methyl, 3-C$_2$H$_5$O, 2-CH$_3$O phenyl | —COOCH$_3$ | M.p. 148–150° C. |
| 6 | 4-methyl, 3-C$_2$H$_5$O, 2-C$_2$H$_5$O phenyl | The same as above | M.p. 122–123° C. |
| 7 | 4-methyl, methylenedioxyphenyl | The same as above | M.p. 139–141° C. |
| 8 | 4-methyl, methylenedioxyphenyl | The same as above | M.p. 186° C. |
| 9 | 4-methyl, 3-CH$_3$O, 2-CH$_3$O, CH$_3$O phenyl | —COOCH$_3$ | M.p. 142–143° C. |

TABLE 1-continued

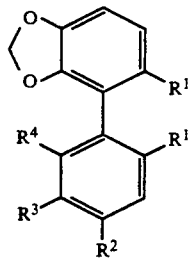

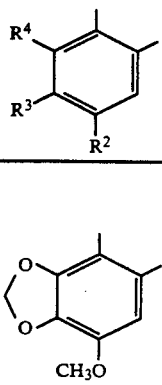

| Ex. No. | R² | R¹ R³ R⁴ | Physical properties, etc. |
|---|---|---|---|
| 10 | 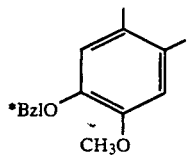 | The same as above | M.p. 131° C. |
| 11 | *BzlO | The same as above | IR $\nu_{Max}^{Nujol}$ (cm$^{-1}$): 1700 Mass (M+): 450 (m/e) |

*Bzl means a benzyl group.

EXAMPLE 12

(1-a) To 5,6-methylenedioxy-4',5'-dimethoxy-2'-(2-hydroxymethylphenyloxycarbonyl)-2-biphenylcarboxylic acid lactone (4 g) are added methanol (100 ml) and an aqueous solution (50 ml) of potassium hydroxide (4 g). The mixture is refluxed for 30 minutes, and concentrated under reduced pressure to remove methanol. The pH of the resulting aqueous solution is adjusted at 1 with 10% hydrochloric acid. The products are extracted with ethyl acetate. The extract is washed, dried and concentrated to dryness under reduced pressure. The residue is triturated with diisopropyl ether to give 5,6-methylenedioxy-4',5'-dimethoxy-2,2'-biphenyldicarboxylic acid (2.84 g). M.p. 207°-210° C.

(1-b) 5,6-Methylenedioxy-4',5'-dimethoxy-2,2'-biphenyldicarboxylic acid trimethylene ester is treated in the same manner as in the above (1-a) to give 5,6-methylenedioxy-4',5'-dimethoxy-2,2'-biphenyldicarboxylic acid (1.4 g).

This product has the same physicochemical properties as those of the product in (1-a).

(2) The product obtained in (1-a) or (1-b) (1.3 g) is dissolved in dioxane (10 ml). To the solution are added thionyl chloride (1.76 ml) and dimethylformamide (0.2 ml), and the mixture is refluxed for one hour. The solvent is distilled off from the reaction mixture, and the residue is dissolved in tetrahydrofuran (100 ml). The solution is added with stirring to a mixture of diethylamine hydrochloride (2.06 g), triethylamine (2.8 ml) and tetrahydrofuran (50 ml). The mixture is stirred at room temperature overnight and concentrated to dryness under reduced pressure. The residue is poured into a mixture of ethyl acetate and water, and the organic layer is separated. The organic layer is washed, dried and distilled to remove the solvent. The residue is recrystallized from a mixture of diethyl ether and hexane to give N,N,N',N'-tetraethyl-5,6-methylenedioxy-4',5'-dimethoxy-2,2'-biphenyldicarboxamide (1.23 g) as colorless crystal. m.p. 148°-149° C.

EXAMPLE 13

(1) 2-Iodo-3,4-methylenedioxybenzoic chloride is treated in the same manner as in Example 1-(3) and -(4) to give 5,6-methylenedioxy-5',6'-methylenedioxy-2'-(2-hydroxy-methylphenyloxycarbonyl)-2-biphenylcarboxylic acid lactone. M.p. 249°-252° C.

(2) The product obtained in (1) (4 g) is treated in the same manner as in Example 12-(1-a) to give 5,6-methylenedioxy-5',6'-methylenedioxy-2,2'-biphenyldicarboxylic acid (2.1 g). M.p. 253°-255° C.

(3) The product obtained in (2) (20 g) is suspended in dioxane. Thereto is added thionyl chloride (20 ml), and the mixture is refluxed. The solvent is distilled off under reduced pressure from the reaction mixture, and the residue is subjected to azeotropic distillation with toluene and then dissolved in dioxane (200 ml). To the solution is added dropwise conc. aqueous ammonia (200 ml) at −20° C, and the mixture is stirred at room temperature overnight. The solvent is distilled off from the reaction mixture, and the residue is adjusted to pH 2 with conc. hydrochloric acid. The precipitated crystals are separated by filtration, washed with water, and then recrystallized from methanol to give 5,6-methylenedioxy-5',6'-methylenedioxy-2,2'-biphenyldicarboxamide (11 g) as colorless crystal. M.p. 249°-250° C.

EXAMPLES 14 TO 16

The corresponding starting compounds are treated in the same manner as in Example 12 or 13-(2) and -(3) to give the compounds as shown in Table 2.

TABLE 2

| Ex. No. | R² | R¹ | Physical properties etc. |
|---------|----|----|--------------------------|
| 14 | (2,5-dimethyl-3,4-dimethoxyphenyl; CH₃O, CH₃O substituents) | both —CONHC(CH₃)₂CH₂OH | M.p. 182–184° C. |
| 15 | The same as above | both —CONHC₂H₅ | M.p. 196–197° C. |
| 16 | (methyl-substituted methylenedioxyphenyl) | both —CONHC(CH₃)₂CH₂OH | M.p. 173–175° C. |

EXAMPLE 17

N,N'-Bis(3-hydroxy-2-methylpropan-2-yl)-5,6-methylenedioxy-5',6'-methylenedioxy-2,2'-diphenyl-dicarboxyamide (3 g) is added to thionyl chloride (20 ml), and the mixture is stirred at room temperature for 2 hours. The reaction mixture is distilled under reduced pressure to remove thionyl chloride, and the residue is dissolved in ethyl acetate. The solution is washed, dried and distilled to remove the solvent, and the residue is crystallized from diisopropyl ether to give 5,6-methylenedioxy-5',6'-methylenedioxy-2,2'-bis(4,4-dimethyl-4,5-dihydro-2-oxazolyl)biphenyl (2 g) as colorless crystal. M.p. 152°–4° C.

EXAMPLE 18

5,6-Methylenedioxy-5',6'-methylenedioxy-2,2'-biphenyldicarboxamide (8 g) is refluxed in phosphorus oxychloride (70 ml) for 4 hours. The reaction mixture is cooled and then poured into ice water. The precipitated crystals are separated by filtration and dissolved in chloroform. The solution is washed with water, dried and distilled to remove the solvent to give 5,6-methylenedioxy-5',6'-methylenedioxy-2,2'-biphenyldicarbonitrile (6.5 g) as colorless crystal. M.p. 213°–215° C.

EXAMPLE 19

5,6-Methylenedioxy-5',6'-methylenedioxy-2,2'-biphenyldicarbonitrile (5 g) is suspended in a mixture of pyridine (100 ml) and dioxane (100 ml), and thereto is added triethylamine (4.7 ml) and further hydrogen sulfide gas is passed through the mixture over a period of 5 hours. The reaction vessel is sealed and allowed to stand at room temperature for 2 hours. The reaction mixture is distilled under reduced pressure to remove the solvent. The residue is extracted with chloroform, and water is added to the extract. The precipitated crystals are separated by filtration to give 5,6-methylenedioxy-5',6'-methylenedioxy-2,2'-biphenylbis(thiocarboxamide) (5.5 g). M.p. 237°–238° C. (decomp.)

EXAMPLE 20

Dimethyl 5,6-methylenedioxy-4'-methoxy-5'-benzoyloxy-2,2'-biphenyldicarboxylate (1.15 g) is dissolved in tetrahydrofuran (50 ml) and methanol (50 ml), and the solution is stirred under 40 psi hydrogen gas atmosphere in the presence of palladium-carbon (0.2 g) for 16 hours. After the reaction, the catalyst is filtered off, and the filtrate is evaporated into dryness under reduced pressure. The residue is treated with methanol to give dimethyl 5,6-methylenedioxy-4'-methoxy-5'-hydroxy-2,2'-biphenyl-dicarboxylate (0.86 g) as colorless crystal. M.p. 172°–173° C.

What is claimed is:

1. A biphenyl derivative of the formula:

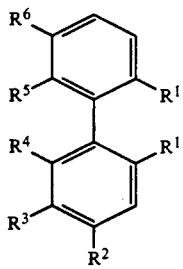 (I)

wherein $R^1$ is an aminocarbonyl group having optionally one or two substituents selected from the group consisting of a hydroxy(lower)alkyl group and a lower alkyl group; an aminothiocarbonyl group; or a cyano group;

among $R^2$ to $R^4$, one of $R^2$ and $R^4$ is hydrogen and the remaining two groups are lower alkoxy groups or both combine to form a lower alkylenedioxy group; and $R^5$ and $R^6$ combine to form a lower alkylenedioxy group.

2. A compound in accordance with claim 1, wherein $R^2$ and $R^3$ are each a lower alkoxy group and $R^4$ is hydrogen.

3. A compound in accordance with claim 1, wherein $R^2$ is hydrogen and $R^3$ and $R^4$ combine to form a lower alkylenedioxy group.

* * * * *